United States Patent [19]

Saito et al.

[11] Patent Number: 4,510,329

[45] Date of Patent: Apr. 9, 1985

[54] PROCESS FOR PREPARING CYCLOPENTENOLONES

[75] Inventors: Kenji Saito, Toyonaka; Hiroshi Yamachika, Ibaraki, both of Japan

[73] Assignee: Sumitomo Chemical Company, Limited, Osaka, Japan

[21] Appl. No.: 211,225

[22] Filed: Nov. 28, 1980

[30] Foreign Application Priority Data

Dec. 7, 1979 [JP] Japan .............................. 54-159454
May 26, 1980 [JP] Japan .............................. 55-70456
Jul. 11, 1980 [JP] Japan .............................. 55-95368

[51] Int. Cl.$^3$ .............................................. C07C 45/59
[52] U.S. Cl. .................................. 568/310; 568/322; 568/341; 568/361
[58] Field of Search ............. 568/310, 322, 341, 361

[56] References Cited

U.S. PATENT DOCUMENTS 3,932,511  1/1976  Muller ............................ 568/341
3,981,920  9/1976  Buchi ............................. 568/379

FOREIGN PATENT DOCUMENTS 21146   8/1976  Japan .
127462  3/1978  Japan .

OTHER PUBLICATIONS

Piancatelli, G. et al., *Tetrahedron*, vol. 34, (1978), pp. 2775–2778.
Scettri et al., *Tetrahedron*, vol. 35, pp. 135–138, (1979).
Piancatelli et al., *Tetrahedron*, vol. 36, pp. 661–663, (1980).
Floyd, *J. Org. Chem.*, 43, pp. 1641–1643, 1978.
Seebach et al., *Angew Chem.*, 89, pp. 334–335, 1977.
Piancatelli et al., *Tetrahedron Letters*, 13, pp. 1131–1134, 1977.
Stork et al., *J. Am. Chem. Soc.*, 97, pp. 3258–3260, 1975.
Piancatelli et al., *Synthesis*, pp. 116–117, 1976.
Piancatelli et al., *Tetrahedron Letters*, 39, pp. 3555–3558, 1976.

*Primary Examiner*—James H. Reamer
*Attorney, Agent, or Firm*—Birch, Stewart, Kolasch & Birch

[57] ABSTRACT

A process for preparing cyclopentenolones of the formula

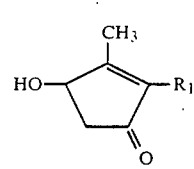

wherein $R_1$ is an alkyl group having not more than 6 carbon atoms, an alkenyl or alkynyl group having not more than 6 carbon atoms or a group of the formula:

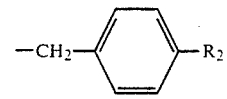

in which $R_2$ is a hydrogen atom, a methyl group or a halogen atom directly from the corresponding furan-carbinols of the formula:

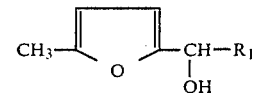

wherein $R_1$ is as defined above in a single step with an excellent yield, characterized in that the furan-carbinols are treated with water in the presence or absence of a catalyst.

5 Claims, No Drawings

PROCESS FOR PREPARING CYCLOPENTENOLONES

The present invention relates to a process for preparing cyclopentenolones. More particularly, it relates to a novel and improved process for preparing cyclopentenolones of the formula:

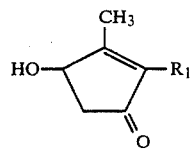 (I)

wherein $R_1$ is an alkyl group having not more than 6 carbon atoms (e.g. methyl, ethyl, propyl, hexyl, cyclopentyl, cyclohexyl), an alkenyl or alkynyl group having not more than 6 carbon atoms (e.g. allyl, α-methylallyl, 4-pentenyl, propargyl) or a group of the formula:

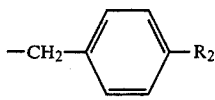

wherein $R_2$ is a hydrogen atom, a methyl group or a halogen atom (e.g. chlorine, bromine, fluorine).

The cyclopentenolones (I) are useful as the alcoholic components of agricultural chemicals. For their production, various methods are known, some of which are industrially adopted. But, they are still not satisfactory in respect to the yield, the complexity of operations, the problems of environmental pollution, etc. Among the known methods, there is included the one in which a furan-carbinol is used as the starting material [G. Piancatelli et al.: Tetrahedron, 34, 2775–2778 (1978)]. In this method, a 4-substituted-5-hydroxy-5-methyl-3-oxycyclopentene derivative is prepared in the following manner:

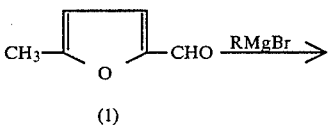

(1)

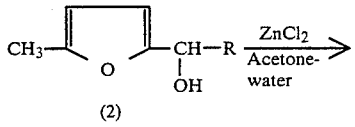

(2)

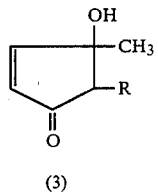

(3)

wherein R is allyl, n-butyl, cyclohexyl, phenyl, 2-thienyl or p-tolyl. Piancatelli et al. also reported in said publication that the treatment of the thus prepared compound (3) wherein R is allyl with neutral alumina provides the corresponding cyclopentenolone. However, in the case wherein the substituent R on the 4-position is one of such groups as those defined as $R_1$ of the formula (I), the compounds (3) are obtained in a very low yield even after a prolonged reaction, though those compounds (3) wherein R is an aromatic group such as phenyl or p-tolyl, or a heterocyclic group such as 2-thienyl are readily obtainable in a good yield with a short reaction time as disclosed in Table 1 at page 2776 of said publication. Thus, it may be said that this method is impractical for production of the cyclopentenolones of the formula (I).

As the result of an extensive study, it has now been found that the cyclopentenolones of the formula (I) can be prepared directly from the furan-carbinols of the formula:

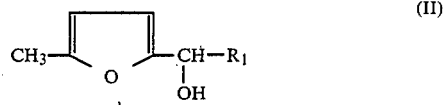 (II)

wherein $R_1$ is as defined above, by a one-step operation in a good yield. The present invention is based on the above finding.

According to the present invention, there is provided a process for preparing the cyclopentenolones (I) from the corresponding furan-carbinols (II), characterized in that the furan-carbinols (II) are treated with water to give directly the corresponding cyclopentenolones (I) in a single step.

The characteristic feature of the process of this invention resides in that the treatment is effected in water. Water may be used alone or contain a small proportion of any organic solvent (e.g. toluene, xylene, diisopropyl ether, benzene, acetone, tetrahydrofuran, dioxane). In this connection, it may be noted that the Piancatelli paper referred to above discloses that the treatment of the furan-carbinol (2) with acetone containing a small proportion of water in the presence of zinc chloride affords the oxo-cyclopentene (3), but it is entirely silient on the production of the cyclopentenolone from the furan-carbinol (2).

In the process of this invention, the starting material is the furan-carbinol (II), which may be prepared by the reaction of 5-methylfurfural with a Grignard reagent of the formula: $R_1MX$ wherein $R_1$ is as defined above, M is Mg, Zn or $Al_{2/3}$ and X is a halogen atom.

On carrying out the process of the invention, the reaction system is preferably adjusted to a certain range of pH for accelerating the reaction rate and suppressing the proceeding of the side reaction, for instance, by the use of a basic and/or acidic substance as such or in solution.

When the reaction is effected at a temperature of about 20° to 120° C., it is desired that the pH is maintained from 3 to 6.5, preferably from 3.5 to 5.8, at the initial stage (i.e. the period until the starting furan-carbinol (II) is consumed). In case of the pH being higher than the said upper limit, the reaction rate becomes markedly small or slow. In case of the pH being lower than the said lower limit, the side reaction proceeds so that the yield of the by-product is increased. At the point that the initial stage ends and the later stage (i.e. the period after the initial stage) starts, the addition of a basic or acidic substance is preferable for attainment of the higher yield of the objective cyclopentenolone (I). In case of using a basic substance, it may be added to the reaction system in such an amount as not to exceed a pH of 10, preferably of 9. In case of using an acidic substance, it may be added to the reaction system to make a concentration of 0.1 to 5N, preferably of 0.2 to 3N. The introduction of a metal salt and/or a surfactant as a catalyst into the reaction system is effective in promoting the reaction rate and increasing the conversion.

When the reaction is effected at a higher temperature, e.g. from 120° to 200° C., the pH of the reaction system may be maintained from 3 to 8 so that the objective cyclopentenolone (I) is easily obtained. In this case too, the introduction of a metal salt and/or a surfactant into the reaction system is effective in promoting the reaction rate and increasing the conversion.

As the basic or acidic substance to be used for regulation of the pH value or to be introduced intermediarily into the reaction system, any usual basic or acidic substance may be employed. Examples of the basic substance are hydroxides of alkali metals (e.g. sodium, potassium) and alkaline earth metals (e.g. calcium, barium), basic salts of said metals such as carbonates, bicarbonates and acetates, amines (e.g. triethylamine, pyridine), basic ion-exchange resins, etc. Examples of the acidic substance are inorganic acids (e.g. sulfuric acid, hydrochloric acid, nitric acid), organic acids (e.g. acetic acid, p-toluenesulfonic acid), acid metal salts (e.g. sodium dihydrogenphosphate, sodium hydrogensulfite), acid ion-exchange resins, etc. Buffer solutions containing these basic or acidic substances are also usable.

The amount of water to be used in the process of the invention may be usually from 0.5 to 200 parts by weight, preferably from 5 to 100 parts by weight, to 1 part by weight of the starting furan-carbinol (II).

Examples of the metal salt usable as the catalyst are magnesium chloride, magnesium bromide, magnesium sulfate, magnesium nitrate, manganese chloride, manganese nitrate, copper sulfate, cobalt acetate, zinc chloride, etc. The amount of the metal salt is usually from 0.001 to 100 mol, preferably from 0.01 to 10 mol, to 1 mol of the furan-carbinol (II). As the surfactant which serves as the catalyst, any of the cationic and amphoionic surfactants may be employed. The amount of the surfactant is usually 0.1 to 20% by weight, preferably 1 to 5% by weight, with respect to the furan-carbinol (II).

One of the typical procedures for carrying out the process of this invention comprises adding the furan-carbinol (II) to an aqueous medium adjusted to a pH of 3 to 6.5, which may optionally contain a catalyst, and effecting the reaction at a temperature of 20° to 120° C. while maintaining the pH between 3 and 6.5 for 30 minutes to 30 hours. Another typical procedure comprises adding the furan-carbinol (II) to an aqueous medium adjusted to a pH of 3 to 6.5 and kept at a temperature of 20° to 120° C., which may optionally contain a catalyst, adding a basic or acidic substance thereto after the consumption of the furan-carbinol (II), and effecting the reaction for 30 minutes to 30 hours. A further typical procedure comprises adding the furan-carbinol (II) to an aqueous medium adjusted to a pH of 3 to 8, which may optionally contain a catalyst, and effecting the reaction at a temperature of 120° to 200° C. for 30 minutes to 30 hours while maintaining the pH between 3 and 8.

The present invention will be hereinafter explained further in detail by the following Examples.

EXAMPLE 1

In a reaction vessel, water (500 ml), 5-methyl-2-furylallylcarbinol (12.5 g) and anhydrous sodium acetate (0.17 g) were charged, and the temperature was elevated to reflux. The pH value was regulated to 5.0 with an aqueous $\frac{1}{3}$N acetic acid solution, and the mixture was stirred under reflux for 12 hours. Then, the pH value was adjusted to 7.9 with an aqueous $\frac{1}{3}$N NaOH solution, and stirring under reflux was continued for 2 hours while maintaining the pH value of 7.8 to 7.9 by the addition of an aqueous $\frac{1}{3}$N acetic acid solution and an aqueous $\frac{1}{3}$N NaOH solution. After cooling, sodium chloride (100 g) was added thereto, and the mixture was extracted with toluene (100 ml) five times. The extract was concentrated at 60° C. under reduced pressure to remove toluene, whereby an oily substance (11.3 g) was obtained. The crude product was subjected to distillation (130°–132° C./1.2 mmHg) to obtain 2-allyl-3-methyl-4-hydroxy-2-cyclopentenolone (10.0 g). Yield, 80.0%.

EXAMPLE 2

In a reaction vessel, water (200 ml) and 5-methyl-2-furylpropargylcarbinol (5 g) were charged, and the pH value was adjusted to 4 with an aqueous $\frac{1}{3}$N NaOH solution and an aqueous $\frac{1}{3}$N HCl solution. The temperature was elevated to 100° C. to reflux, and the mixture was stirred under reflux for 16 hours while maintaining the pH value of 3.8 to 4.1 by the addition of an aqueous $\frac{1}{3}$N NaOH solution and an aqueous $\frac{1}{3}$N HCl solution. Then, the pH value was adjusted to 8.0 with an aqueous $\frac{1}{3}$N NaOH solution, and stirring under reflux was continued for 4 hours while maintaining the pH value of 7.5 to 8.0 by the addition of an aqueous $\frac{1}{3}$N NaOH solution and an aqueous $\frac{1}{3}$N HCl solution. After cooling, sodium chloride (70 g) was added, and the mixture was extracted with toluene (100 ml) four times. The extract was concentrated at 60° C. under reduced pressure to remove toluene, whereby an oily substance (4.7 g) was obtained. The crude product was purified by column chromatography with silica gel (60 g) (developing solvent, ethyl acetate-n-hexane (1:2 by volume)) to obtain 2-propargyl-3-methyl-4-hydroxy-2-cyclopentenone (3.4 g). Yield, 68%.

EXAMPLE 3

In a reaction vessel, water (100 ml) and 5-methyl-2-furylmethylcarbinol (5 g) were charged, and the pH value was adjusted to 5.5 with an aqueous $\frac{1}{3}$N NaOH solution and an aqueous $\frac{1}{3}$N HCl solution. The temperature was elevated up to 100° C. to reflux, and the mixture was stirred under reflux for 16 hours while maintaining the pH value of 4.0 to 5.7 by the addition of an aqueous $\frac{1}{3}$N NaOH solution and an aqueous $\frac{1}{3}$N HCl solution. After cooling to 50° C., concentrated hydrochloric acid (10 g; corresponding to 0.9N) was added, and stirring was continued at 50° C. for 22 hours. After cooling, the reaction mixture was neutralized with an aqueous 20% NaOH solution and an aqueous $\frac{1}{3}$N NaOH solution. Then, sodium chloride (30 g) was added thereto, and the mixture was extracted with toluene (50 ml) five times. The extract was concentrated at 60° C. under reduced pressure to remove toluene, whereby an oily substance (4.4 g) was obtained. The crude product was subjected to column chromatography with silica gel (60 g) (developing solvent, ethyl acetate-n-hexane (1:2 by volume)), and the objective fraction was concentrated to obtain 2-methyl-3-methyl-4-hydroxy-2-cyclopentenone (3.2 g). Yield, 64%.

EXAMPLE 4

In a reaction vessel, water (100 ml) was charged, and MgCl$_2$.6H$_2$O (6.8 g) was dissolved therein. Then, 5-methyl-2-furylpropargylcarbinol (5 g) was added thereto, and the temperature was elevated up to 100° C. to reflux. The pH value was adjusted to 3.8 to 4.1 with an aqueous 1N HCl solution and an aqueous 1N NaOH solution, and the mixture was stirred under reflux for 8 hours. Then, the pH was adjusted to 7.3 with an aqueous 1N NaOH solution, and stirring under reflux was continued for 8 hours. After cooling to 40° C., sodium chloride (35 g) was added, and the mixture was extracted with toluene (50 ml) four times. The extract was dried over anhydrous magnesium sulfate and concentrated at 60° C. under reduced pressure to remove toluene, whereby an oily substance (4.6 g) was obtained. The crude product was subjected to column chromatography with silica gel (60 g) and a mixture of ethyl acetate-n-hexane (1:2 by volume) as the developing solvent. Firstly, substances having high boiling points flowed out, then a small amount of unreacted 5-methyl-2-furylpropargylcarbinol came out, and after a considerably long time, the objective 2-propargyl-3-methyl-4-hydroxy-2-cyclopentenone flowed out. The objective fraction was concentrated to obtain 2-propargyl-3-methyl-4-hydroxy-2-cyclopentenone (3.3 g). Yield, 66%.

EXAMPLE 5

In a reaction vessel, water (1 liter), 5-methyl-2-furylallylcarbinol (25 g), anhydrous sodium acetate (0.4 g) and dodecyltrimethylammonium chloride (770 mg) were charged, and the temperature was elevated to reflux. The pH value was adjusted to 5.2 with acetic acid, and the mixture was stirred under reflux for 6 hours. Then, the pH value was adjusted to 7.8 with an aqueous 1N NaOH solution, and stirring was continued under reflux for 2 hours while maintaining the pH value of 7.8 to 7.5. After cooling, sodium chloride (300 g) was added thereto, and the mixture was extracted with toluene (200 ml) five times. The extract was concentrated at 60° C. under reduced pressure to remove toluene, whereby an oily substance (22.7 g) was obtained. The crude product was purified by distillation (130°–132° C./1.2 mmHg) to obtain 2-allyl-3-methyl-4-hydroxy-2-cyclopentenolone (21.2 g). Yield, 80.0%.

EXAMPLE 6

In a reaction vessel, 5-methyl-2-furylpropylcarbinol (1 g) was charged, and a solution of ZnCl$_2$ (0.9 g) in water (40 ml) was added. The temperature was elevated up to 100° C. to reflux, and several drops of an aqueous 0.1N NaOH solution were added thereto to adjust the pH value to 4.5. By further addition of the same NaOH solution (0.3 ml) thereto, the pH value was not changed but remained at 4.5. The mixture was stirred under reflux for 11 hours, whereby the pH value became 4.2. After cooling, sodium chloride (12 g) was added thereto, and the mixture was extracted with toluene (30 ml) four times. The extract was concentrated at 60° C. under reduced pressure to remove toluene, and the resultant residue was subjected to chromatography with silica gel (10 g) and a mixture of ethyl acetate-n-hexane (1:2 by volume) as the developing solvent to obtain 2-propyl-3-methyl-4-hydroxy-2-cyclopentenone (0.57 g). Yield, 57%.

EXAMPLE 7

Potassium secondary phosphate (1.12 g) and potassium primary phosphate (3.54 g) were dissolved in water (800 ml) to prepare a buffer solution (pH 6.2, 20° C.). In a reaction vessel, 5-methyl-2-furylallylcarbinol (20 g) and the entire amount of the buffer solution as prepared above were charged, and the temperature was elevated up to 150° C. in 35 minutes while stirring. The mixture was stirred at the same temperature for 4 hours, the inner pressure at this time being 3.8 kg/cm$^2$. After cooling with ice, sodium chloride (100 g) was added thereto, and the mixture was extracted with methyl isobutyl ketone (200 ml) four times. The extract was concentrated at 60° C. under reduced pressure to remove methyl isobutyl ketone, whereby an oily substance (18.2 g) was obtained. The crude product was purified by distillation (130°–132° C./1.2 mmHg) to obtain 2-allyl-3-methyl-4-hydroxy-2-cyclopentenone (16.6 g). Yield, 83%.

EXAMPLE 8

A buffer solution was prepared by dissolving potassium secondary phosphate (4 g) in water (800 ml) and adjusting the pH value to 7.5 (25° C.) with phosphoric acid. In a reaction vessel, 5-methyl-2-furyl-(α-methylallyl)-carbinol (20 g) and the entire amount of the buffer solution as prepared above were charged, and the temperature was elevated up to 180° C. in 55 minutes while stirring. The mixture was stirred at the same temperature for 5 hours, the inner pressure at this time being 9 kg/cm$^2$. After ice-cooling, sodium chloride (100 g) was added thereto, and the mixture was extracted with methyl isobutyl ketone (200 ml) four times. The extract was concentrated at 60° C. under reduced pressure to remove methyl isobutyl ketone, and the resultant residue was subjected to distillation (112°–117° C./0.3 mmHg) to obtain 2-(α-methylallyl)-3-methyl-4-hydroxy-2-cyclopentenone (15.3 g). Yield, 76.5%. NMR spectrum (CDCl$_3$ internal standard; TMS, δppm, 60 MHz): 5.99 (complex m, 1H,

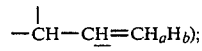

);

5.08 (m, 1H,

);

4.84 (m, 1H,

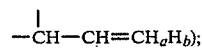

);

4.63 (broad d, 1H, 4-H); 3.33 (m, 2H, 4-OH and

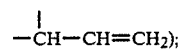

);

2.73 (dd, 1H, 5-H); 2.21 (dd, 1H, 5-H); 2.08 (s, 3H, 3-CH$_3$); 1.21 (d, 3H,

—CH—CH=CH$_2$).
|
CH$_3$

EXAMPLE 9

A buffer solution was prepared by dissolving sodium acetate (1.03 g) and MgCl$_2$.6H$_2$O (0.27 g) in water (200 ml) and adjusting the pH value to 6.0 (20° C.) with acetic acid. In a reaction vessel, 5-methyl-2-furylallylcarbinol (5 g) and the entire amount of the buffer solution as prepared above were charged, and the temperature was elevated up to 150° C. in 35 minutes while stirring. The mixture was stirred at the same temperature for 3 hours. After ice-cooling, sodium chloride (50 g) was added, and the mixture was extracted with methyl isobutyl ketone (100 ml) four times. The extract was concentrated at 60° C. under reduced pressure to remove methyl isobutyl ketone, whereby an oily substance (4.6 g) was obtained. The crude product was purified by column chromatography with silica gel (60 g) (developing solvent, ethyl acetate-n-hexane (1:2 by volume)) to obtain 2-allyl-3-methyl-4-hydroxy-2-cyclopentenone (4.0 g). Yield, 80%.

EXAMPLE 10

A buffer solution was prepared by dissolving sodium acetate (1.03 g) and Paion D-408 (polyoxyethylene alkyl phenyl ether; manufactured by Takemoto Yushi Inc.) (0.44 g) in water (200 ml) and adjusting the pH value to 6.0 with acetic acid. In a reaction vessel, 5-methyl-2-furylallylcarbinol (5 g) and the entire amount of the buffer solution as prepared above were charged, and the temperature was elevated up to 150° C. in 35 minutes while stirring. The mixture was stirred at the same temperature for 3.5 hours. After ice-cooling, sodium chloride (50 g) was added, and the mixture was extracted with methyl isobutyl ketone (100 ml) four times. The extract was concentrated at 60° C. under reduced pressure to remove methyl isobutyl ketone, whereby an oily substance (4.6 g) was obtained. The crude product was purified by column chromatography with silica gel (60 g) (developing solvent, ethyl acetate-n-hexane (1:2 by volume)) to obtain 2-allyl-3-methyl-4-hydroxy-2-cyclopentenone (4.2 g). Yield, 84%.

EXAMPLES 11 AND 12

Using the furan-carbinol (II) (5 g), the corresponding cyclopentenolone (I) was prepared in the same manner as in Example 2 under the conditions shown in the following Table:

| Example No. | R$_1$ | Initial stage pH | Time | Later stage pH | Basic substance | Time | Yield (%) |
|---|---|---|---|---|---|---|---|
| 11 | n-Hexyl | 4.0–5.6 | 30 | 7.3–7.5 | 5% Aqueous sodium acetate solution | 3 | 77 |
| 12 | p-Methylbenzyl | 4.0–5.7 | 30 | 7.3–7.5 | 5% Aqueous potassium secondary phosphate solution | 3 | 81 |

EXAMPLES 13 AND 14

Using the furan-carbinol (II) (5 g), the corresponding cyclopentenolone (I) was prepared in the same manner as in Example 3 under the conditions shown in the following Table:

| Example No. | R$_1$ | Initial stage pH | Time | Later stage Acidic substance and its amount | Time | Yield (%) |
|---|---|---|---|---|---|---|
| 13 | Allyl | 5.0–5.5 | 8 | Conc. nitric acid, 6 g | 22 | 78 |
| 14 | Benzyl | 4.0–5.4 | 30 | Conc. hydrochloric acid, 10 g | 22 | 84 |

EXAMPLES 15 TO 22

Using the furan-carbinol (II) (5 g), the corresponding cyclopentenolone (I) was prepared in the same manner as in Example 4 under the conditions shown in the following Table:

| Example No. | R$_1$ | Amount of MgCl$_2$.6H$_2$O (g) | Initial pH | Later pH | Yield (%) |
|---|---|---|---|---|---|
| 15 | Methyl | 8.1 | 4.0–5.7 | 7.3 | 63 |
| 16 | Propyl | 6.6 | 4.0–5.6 | 7.5 | 71 |
| 17 | n-Hexyl | 5.2 | 4.0–5.6 | 7.4 | 75 |
| 18 | Cyclohexyl | 5.2 | 4.0–5.4 | 7.3 | 75 |
| 19 | 4-Pentenyl | 5.6 | 4.0–5.8 | 7.3 | 82 |
| 20 | p-Chlorobenzyl | 4.3 | 4.0–5.7 | 7.2 | 88 |
| 21 | Benzyl | 5.0 | 4.0–5.4 | 7.5 | 84 |
| 22 | p-Methylbenzyl | 4.7 | 4.0–5.3 | 7.3 | 80 |

EXAMPLES 23 TO 28

Using the furan-carbinol (II) (5 g), the corresponding cyclopentenolone (I) was prepared in the same manner as in Example 7 under the conditions shown in the following Table:

| Example No. | R$_1$ | Reaction time (hr) | Reaction temperature (°C.) | Yield (%) |
|---|---|---|---|---|
| 23 | Propyl | 1.5 | 180 | 66 |
| 24 | Propargyl | 1.0 | 180 | 64 |
| 25 | Cyclohexyl | 1.5 | 180 | 75 |
| 26 | Benzyl | 6.0 | 150 | 85 |
| 27 | p-Methylbenzyl | 6.0 | 150 | 80 |
| 28 | p-Chlorobenzyl | 6.0 | 150 | 80 |

What is claimed is:

1. A one-step process for preparing a cyclopentenolone which consists essentially of treating a furan-carbinol of the formula:

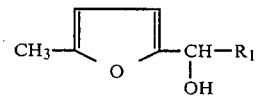

wherein R$_1$ is an alkyl group having not more than 6 carbon atoms, an alkenyl or alkynyl group having not more than 6 carbon atoms or a group of the formula:

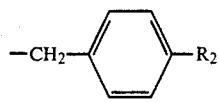

in which R₂ is a hydrogen atom, a methyl group or a halogen atom at a temperature of 120° to 200° C. in an aqueous medium at a pH of 3 to 8 in the presence or absence of a catalyst to obtain the corresponding cyclopentenolone of the formula:

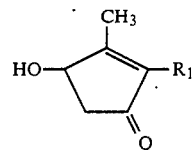

wherein $R_1$ is as defined above.

2. The process according to claim 1, wherein the pH value of the aqueous medium at the initial stage of the reaction is 3 to 6.5, and a basic or acidic substance is added to the reaction system at the later stage of the reaction.

3. The process according to claim 2, wherein a metal salt and/or a surfactant are added to the reaction system as the catalyst.

4. The process according to claim 1, wherein the pH value of the aqueous medium is 3 to 6.5, and a metal salt is added to the reaction system as the catalyst.

5. The process according to claim 1, wherein a metal salt and/or a surfactant are added to the reaction system as the catalyst.

* * * * *